United States Patent
Van Ginkel et al.

(10) Patent No.: US 6,720,442 B2
(45) Date of Patent: Apr. 13, 2004

(54) PREPARATION OF PHOSPHORUS-CONTAINING COMPOUNDS USEFUL IN THE PREPARATION OF BIPHOSPHINE LIGANDS

(75) Inventors: Roelof Van Ginkel, Amsterdam (NL); Alexander Van Der Made, Amsterdam (NL); Jan De With, Amsterdam (NL); Wolf Eilenberg, deceased, late of Oegstgeest (NL), by Ursula Eilenberg-Robben, legal representative

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 10/346,297

(22) Filed: Jan. 15, 2003

(65) Prior Publication Data

US 2003/0109754 A1 Jun. 12, 2003

Related U.S. Application Data

(62) Division of application No. 09/762,264, filed as application No. PCT/EP99/05748 on Aug. 3, 1999, now Pat. No. 6,548,708.

(30) Foreign Application Priority Data

Aug. 5, 1998 (EP) ............................................. 98306254
Oct. 23, 1998 (EP) ............................................. 98203587

(51) Int. Cl.$^7$ .................................................. C07F 9/02
(52) U.S. Cl. ........................... 558/134; 568/10; 568/12; 564/12
(58) Field of Search .............................. 568/10, 12, 16, 568/17, 14; 564/12; 558/70, 73, 134

(56) References Cited

U.S. PATENT DOCUMENTS

| | | | |
|---|---|---|---|
| 3,131,204 A | | 4/1964 | Sisler et al |
| 4,006,187 A | | 2/1977 | Kamienski et al. |
| 4,698,447 A | * | 10/1987 | Blum .......................... 568/12 |
| 5,354,894 A | | 10/1994 | Devon |
| 6,437,164 B1 | * | 8/2002 | Yamamoto et al. ........... 558/71 |

FOREIGN PATENT DOCUMENTS

| | | |
|---|---|---|
| EP | 0364046 A2 | 4/1990 |
| EP | 0391329 A2 | 10/1990 |
| EP | 0754695 A1 | 1/1997 |
| FR | 1515582 | 3/1968 |
| JP | 72047014 | 3/1970 |
| NL | 8800349 | 9/1989 |
| WO | WO 92/19622 | 11/1992 |
| WO | WO 97/37765 | 10/1997 |

OTHER PUBLICATIONS

CA:110:114326 abs of Zhurnal Oganicheskoi Khimii by Kohl et al 24(5) pp 1109–1110 1988.*
CA:103:214884 abs of J. Chem Soc. Dalton Trans. by Bard et al (7) pp 1303–7 1985.*
Inorganic Chemistry vol. 36 No. 18 by Poetschke et al pp 4087–4093 1997.*
CA:129:28000 abs of Russian Chemical Bulletin by Kabachnik et al 47(2) pp 332–339 1998.*
CA:102:149449 abs of Journal of Amer. Chem. Soc. by DePue et al 107(7) pp 2131–7 1985.*
CA:128:217443 abs of European Journal of Inorganic Chemistry by Ebels et al (3) pp 331–337 1998.*
Schmidbaur et al. (1983), "Rearrangements of the Methyltrimesitylphosphonium and Methylenebis(methyldimesitylphosphonium) Cation Skeletons on Treatment with Base," *Chem. Ber.* 116(5):1947–1954, abstract only (Abstract No. CA:99:38552).

* cited by examiner

*Primary Examiner*—Jean F. Vollano
(74) *Attorney, Agent, or Firm*—Reed & Eberle LLP

(57) ABSTRACT

This invention relates to processes for making phosphorus compounds $R_2P$—X—$PR_2$, $R_2P$-M, $R_2P$-L and $R_3P$, and the novel cation $R_2P^+(L)$-X—$P^+(L)R_2$, where R represents an optionally substituted hydrocarbyl group, X represents a bridging group, L represents a leaving group and M represents an alkali metal atom. The invention relates further to a process for making a compound $R_2P$-L from a compound R—H via a new process for making the compound R—Li followed by its reaction with a compound $Hal_2P$-L. The compound $R_2P$—X—$PR_2$ is a ligand suitable for making catalysts for copolymerizing carbon monoxide and a olefinically unsaturated compound.

10 Claims, No Drawings

PREPARATION OF PHOSPHORUS-CONTAINING COMPOUNDS USEFUL IN THE PREPARATION OF BIPHOSPHINE LIGANDS

CROSS REFERENCE TO RELATED APPLICATIONS

This application is a divisional of U.S. Ser. No. 09/762,264, filed on Feb. 2, 2001 now U.S. Pat. No. 6,548,708, which is a 371 application of PCT/EP99/05748, filed on Aug. 3, 1999.

FIELD OF THE INVENTION

This invention relates to processes for making phosphorus-containing compounds; to novel phosphorus-containing compounds themselves; to a process for making lithiated compounds useful in the aforesaid processes; to the use of phosphorus-containing compounds produced by the aforesaid processes, in the preparation of polymerization catalyst compositions; to the use of said catalyst compositions in the preparation of polymers; and to polymers thereby produced.

BACKGROUND OF THE INVENTION

The invention concerns particularly though not exclusively, processes for the preparation of phosphorus-containing compounds useful in the preparation of catalyst compositions which facilitate the copolymerization of carbon monoxide with an olefinically unsaturated compound to make linear alternating copolymers.

Such copolymers and catalyst compositions are described, for example, in EP-A-121965 and EP-A-248483. To set the present invention in the context in which it was made these copolymers, catalysts, compositions and associated preparative process will now be described but it should be noted that many of the compounds and processes of the present invention, described in detail hereinafter, will be useful also in other contexts.

Broadly, such catalyst compositions comprise a Group VIII (in more modern nomenclature a Group 8, 9 or 10) metal. Examples of suitable Group VIII metals for use in such catalyst compositions are nickel and cobalt. However, the Group VIII metal is preferably a noble Group VIII metal, of which palladium is most preferred.

The Group VIII metal of such a composition is typically employed as a cationic species. As the source of Group VIII metal cations conveniently a Group VIII metal salt is used. Suitable salts include salts of mineral acids, such as sulphuric acid, nitric acid, phosphoric acid, perchloric acid and sulphonic acids, and organic salts, such as acetylacetonates. Preferably, a salt of a carboxylic acid is used, for example a carboxylic acid with up to 8 carbon items, such as acetic acid, trifluoroacetic acid, trichloroacetic acid, propionic acid and citric acid. Palladium (II) acetate and palladium (II) trifluoroacetate represent particularly preferred sources of palladium cations. Another suitable source of Group VIII metal cations is a compound of the Group VIII metal in its zero-valent state.

Such a catalyst composition is preferably based, as an additional component, on a ligand which forms a complex with the Group VIII metal. It would appear that the presence of two complexing sites in one ligand molecule significantly contributes to the activity of the catalysts. It is thus preferred to use a ligand containing at least two dentate groups which can complex with the Group VIII metal. Although less preferred, it is also possible to employ a monodentate ligand, i.e. a compound which contains a single dentate group which can complex with the Group VIII metal, in particular a dentate group of phosphorous. Suitably a bidentate ligand is used which contains two phosphorus-, nitrogen- or sulphur-containing dentate groups. It is also possible to use a mixed bidentate ligand such as 1-diphenylphosphino ethylthiopropane.

DETAILED DESCRIPTION OF THE INVENTION

A preferred bidentate ligand for such a catalyst composition can be indicated by the general formula

$$R_2M^1\text{-}X\text{-}M^2R_2 \qquad (I)$$

In this formula $M^1$ and $M^2$ independently represent a phosphorus, nitrogen, arsenic or antimony atom, each group R independently represents an optionally substituted hydrocarbyl group, in particular of up to 10 carbon atoms, and X represents a bivalent bridging group.

In a ligand of formula (I) each group R may independently represent an optionally substituted alkyl, aryl, aralkyl or cycloalkyl group.

An aryl group R is preferably phenyl.

Generally, unless stated otherwise in this specification, any alkyl group or alkyl moiety of a larger group may be linear or branched and may suitably contain 1 to 10, preferably 1 to 6, and most preferably 1 to 4 carbon atoms, suitable examples being methyl, ethyl and propyl. Generally, unless stated otherwise in this specification, any cycloalkyl group may be monocyclic or polycyclic and may contain 3–15, preferably 3–12, most preferably 3–8 carbon atoms, for example cyclohexyl.

Generally, unless stated otherwise in this specification, preferred substituents for an aryl group or an aryl moiety within a larger group include halogen, especially fluorine, chlorine and bromine atoms, and nitro, cyano, hydroxyl, alkyl, haloalkyl, haloalkoxy, alkoxyalkyl, aryloxy, alkoxy, alkoxyalkoxy, amino, mono-and di-alkylamino, aminoalkyl, mono- and di-alkyl-aminoalkyl, amido, and mono- and di-alkylamido groups.

Generally, unless otherwise stated in this specification, any substituted aryl group may suitably be substituted by 1–3 substituents, preferably by 1 substituent.

Generally, unless stated otherwise in this specification, preferred substituents of an alkyl or cycloalkyl group or of an alkyl or cycloalkyl moiety within a larger group include halogen, especially fluorine, chlorine or bromine atoms, and nitro, cyano, hydroxyl, alkoxy, haloalkoxy, alkoxycarbonyl, and amino and mono- and di-alkylamino groups.

Preferably a hydrocarbyl group R carries a polar moiety. Suitable polar moieties include halogen atoms, especially fluorine and chlorine, haloalkoxy groups, alkoxy groups, such as methoxy and ethoxy groups, amino, mono- and di-alkylamino groups, such as methylamino, dimethylamino and diethylamino groups, aminoalkyl, mono-and dialkylaminoalkyl groups, amido, mono- and di-alkylamido groups, alkoxyalkoxy, alkylthio, alkylsulfonyl, dialkylamidosulfonyl, alkylsulfonate, lithio-oxy, aryloxy groups such as phenoloxy and sulfonates (—$SO_3M$, with M being Li, Na, K or H).

Preferably at least one group R represents an aromatic group, in particular an aromatic group which is polar substituted.

It is preferred that one or more of the groups R in the ligand of formula (I) represents an aryl group, preferably a phenyl group, substituted at an ortho position with respect to M1 or M2 by a polar moiety, preferably an alkoxy group, especially a methoxy group, or an aryloxy group, especially a phenoloxy group.

It is preferred that at least one of the groups R attached to the atom $M^1$, and at least one of the groups R attached to the atom $M^2$, is as defined above, in accordance with any of the definitions given in the preceding three paragraphs. It is preferred that all four groups R are as defined above, in accordance with any of the definitions given in the preceding paragraph.

Preferably all the groups R are identical. In especially preferred ligands each group R is an 2-methoxyphenyl group (hereinafter called 2-anisyl). In another preferred ligand each group R is a 2-phenoxyphenyl group.

In a ligand of formula (I), X preferably represents a bivalent bridging group containing at least 1 bridging atom, preferably containing from 2 to 4 bridging atoms. Bridging atoms may be selected from C, N, O, Si and S atoms. Preferably X is an organic bridging group containing at least one carbon atom. More preferably X is an organic bridging group containing from 2 to 4 bridging atoms, at least two of which are carbon atoms. Examples of such groups R are —$CH_2$—$CH_2$—, —$CH_2$—$CH_2$—$CH_2$, —$CH_2$—CH($CH_3$)—$CH_2$—, —$CH_2$—C($CH_3$)$_2$—$CH_2$—, —$CH_2$—C($C_2H_5$)$_2$—$CH_2$—, —$CH_2$—Si($CH_3$)$_2$—$CH_2$—, —$CH_2$—$CH_2$—$CH_2$—$CH_2$—, —$CH_2$—CH($C_2H_5$)—$CH_2$—, —$CH_2$—CH(n-Pr)—$CH_2$ and —$CH_2$—CH(n-Bu)—$CH_2$—.

In a ligand of formula (I) $M^1$ and $M^2$ preferably represent phosphorus atoms and it is to the preparation of such ligands that certain aspect of the present invention relate.

The amount of a said bidentate ligand supplied may vary considerably, but is usually dependent on the amount of Group VIII metal present in the catalyst composition. Preferred amounts of a said phosphorus-containing bidentate ligand are in the range of from 0.5 to 8, more preferably in the range of from 0.5 to 2 moles per gram atom of Group VIII metal.

Such a Group VIII metal containing catalyst composition may be based on another additional component which functions during the copolymerization as a source of anions which are non- or only weakly coordinating with the Group VIII metal under the conditions of the copolymerization. Typical additional components are, for example, protic acids, salts of protic acids, Lewis acids, acids obtainable by combining a Lewis acid and a protic acid, and salts derivable from such combinations. Suitable are strong protic acids and their salts, which strong protic acids have in particular a pKa of less than 6, more in particular less than 4, preferably less than 2, when measured in aqueous solution at 18° C. Examples of suitable protic acids are the above mentioned acids which may also participate in the Group VIII salts, e.g. perchloric acid and trifluoroacetic acid. Suitable salts of protic acids are, for example, cobalt and nickel salts. Other suitable protic acids are adducts of boric acid and 1,2-diols, catechols or salicylic acids. Salts of these adducts may be used as well. Suitable Lewis acids are, for example, $BF_3$, $AlF_3$, $AsF_5$ and Sn ($CF_3SO_3$)$_2$, and also hydrocarbylboranes, such as triphenylborane, tris-(perfluorophenyl)borane and tris[bis-3,5-(trifluoromethyl)phenyl]borane. Protic acids with which Lewis acids may be combined are for example sulphonic acids and hydrohalogenic acids, in particular HF. A very suitable combination of a Lewis acid with a protic acid is tetrafluoroboric acid ($HBF_4$). Other compounds which function during the copolymerization as a source of anions which are non- or weakly coordinating with the Group VIII metal are salts which contain one or more hydrocarbylborate anions or carborate anions, such as sodium tetrakis[bis-3,5-(trifluoromethyl)phenyl]borate, lithium tetrakis (perfluorophenyl)borate and cobalt carborate ($Co(B_{11}CH_{12})_2$). Again other compounds which may be mentioned in this context are aluminoxanes, in particular methyl aluminoxanes and t-butyl aluminoxanes.

The amount of the additional component which functions during the copolymerization as a source of anions which are non- or only weakly coordinating with the Group VIII metal is preferably selected in the range of 0.1 to 50 equivalents per gram atom of Group VIII metal, in particular in the range of from 0.5 to 25 equivalents per gram atom of Group VIII metal. However, the aluminoxanes may be used in such quantity that the molar ratio of aluminium to the Group VIII metal is in the range of from 4000:1 to 10:1, preferably from 2000:1 to 100:1.

The amount of such a catalyst composition used in the said copolymerization of the invention may vary between wide limits. Recommended quantities of catalyst composition are in the range of 10–8 to 10–2, calculated as gram atoms of Group VIII metal per mole of olefinically unsaturated compound to be copolymerized with carbon monoxide. Preferred quantities are in the range of 10–7 to 3 on the same basis.

Olefinically unsaturated compounds which can be used as monomers in the said copolymerization process include compounds consisting exclusively of carbon and hydrogen and compounds which in addition comprise hetero atoms, such as unsaturated esters, ethers and amides. Unsaturated hydrocarbons are preferred. Examples of suitable olefinic monomers are lower olefins, such as ethene, propene and butene-1, cyclic olefins such as cyclopentene, aromatic compounds, such as styrene and a-methylstyrene and vinyl esters, such as vinyl acetate and vinyl propionate. Most preference is given to ethene and mixtures of ethene with another olefinically unsaturated compound, in particular an α-olefin, such as propene or butene-1. The term "lower" used in this document to specify an organic compound has the meaning that the organic compound contains up to 6 carbon atoms.

Generally, the molar ratio of on the one hand carbon monoxide and on the other hand the olefinically unsaturated compound(s) used as monomer is selected in the range of 1:5 to 5:1. Preferably the molar ration is in the range of 1:2 to 2:1, substantially equimolar rations being preferred most.

A said copolymerization process employing a catalyst composition described above may be carried out in the presence of a liquid diluent, but it may also be carried out as a gas phase process. If it is carried out in the presence of a liquid diluent preferably a liquid diluent is used in which the copolymer to be prepared forms a suspension, in which case a diluent may be selected in which the copolymer is insoluble or virtually insoluble. Examples of liquid diluents are ketones (e.g. acetone), chlorinated hydrocarbons (e.g. chloroform or dichloromethane), aromatics (e.g. toluene, benzene, chlorobenzene) and, preferably, protic diluents, such as lower alcohols (e.g. methanol and ethanol). Mixtures of liquid diluents may be used as well, for example protic diluents may comprise an aprotic diluent.

When a said copolymerization process is carried out as a gas phase process it is preferred to use a catalyst system supported on a solid carrier, usually in order to facilitate the introduction of the catalyst composition into the reactor.

Suitable carrier materials may be inorganic, such as silica, alumina or charcoal, or organic such as cellulose or dextrose. Furthermore a polymer material may be used as carrier, such as polyethene, polypropene or, in particular, copolymers of carbon monoxide with anis ethylenically unsaturated compound, for example linear alternating copolymers of carbon monoxide with ethene or carbon monoxide with ethene and propene or butene-1.

Conveniently the carrier is impregnated with a solution of the catalyst system in a suitable liquid. It will be appreciated that the amount of liquid used is relatively small, so that any excess thereof can easily be removed before or during the initial stage of the copolymerization process. On the other hand it has been observed, that the addition of a minor amount of liquid during the copolymerization process has a delaying effect on the deactivation rate of the catalyst, the quantity of liquid being so small that the gas phase is the continuous phase during the polymerization. The quantity of liquid is in particular selected such that it is 20–80% by weight, more in particular 40–60% by weight, of the quantity which is sufficient to saturate the gas phase under the conditions of the polymerization. Polar liquids are preferred, such as lower alcohols, for example methanol and ethanol, lower ethers such as diethylether, tetrahydrofuran or the dimethylether of diethylene glycol(diglyme) and lower ketones such as acetone and methylethylketone.

The performance of such a Group VIII metal catalyst composition in a said copolymerization process may be improved by introducing an organic oxidant, such as a quinone or an aromatic nitro compound. Preferred oxidants are quinones selected from the group consisting of benzoquinone, napththoquinone and anthraquinone. When the process is carried out as a gas phase process, the quantity of oxidant is advantageously in the range of from 1 to 50, preferably in the range of from 1 to 20 mole per gram atom of metal of Group VIII.

The copolymerization process is usually carried out at a temperature between 20 and 200° C., preferably at a temperature in the range of from 30 to 150° C., and usually applying a pressure between 0.2 and 20 MPa, pressures in the range of from 1 to 10 MPa being preferred.

The copolymer may be recovered from a said polymerization mixture by any suitable conventional technique.

A copolymer thus obtained has typically a limiting viscosity number in the range of 0.1–5 dl/g, in particular 0.5–3 dl/g, based on viscosity measurements at 35° C. of solutions of the copolymers in hexafluoroisopropanol.

A copolymer thus obtained is particularly suitable as a thermoplastic for fibres, films or sheets, or for injection moulding, compression moulding and blow building applications. Such a copolymer may be used for applications in the car industry, for the manufacture of packaging materials for food and drinks and for various uses in the domestic sphere.

As mentioned above, in certain aspects the present invention relates to the preparation of a biphosphine ligand of the general formula $$R_2M^1\text{-}X\text{-}M^2R_2 \quad (I)$$

where $M^1$ and $M2$ both represent phosphorus atoms and R and X are as defined above.

Broadly, two routes have been proposed for the preparation of the biphosphine ligand (I). Both start with a triphosphine compound $R_3P$ (II), prepared for example by reaction of a lithiated compound R—Li (III) with phosphorus trichloride ($PCl_3$). Two compounds $R_3P$ are coupled together via a linkage —X—. Clearly, in making a molecule $R_2P$—X—$PR_2$ from two molecules of $R_3P$, two groups R are removed. It is economically disadvantageous to have to use a molar quantity of the compound R—Li which is at least 50% in excess of the molar quantity of the corresponding anisyl groups represented in the biphosphine ligand (I).

The first prior art route for obtaining a biphosphine ligand (I) starting with a triphosphine compound $R_3P$ (II) is described in EP-A-286196, EP-A-290075 and EP-A-294000. A triphosphine compound $R_3P$ is reacted with metallic sodium in the presence of liquid ammonia to produce a compound of general formula $R_2P$—$Na^+$ (with loss of one group R) which is then reacted with a dihalo compound Hal-X-Hal to provide a biphosphine ligand. A major disadvantage of this process in addition to the inefficient loss of R groups arises from the need to use liquid ammonia, with its attendant handling and recycling difficulties.

The second prior art route for obtaining a biphosphine ligand (I), starting with a triphosphine compound $R_3P$ (II), is described in EP-A-364046. The triphosphine compound $R_3P$ is reacted with a dihalo compound Hal-X-Hal to produce a biphosphine salt of general formula

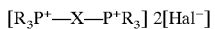

which is reduced by an alkali metal tetrahydride or derivative thereof to make the biphosphine ligand. Disadvantages of this process in addition to the inefficient loss of R groups include the fact that the process, whilst very efficient for biphosphine ligands in which the group —X— is a polymethylene group, is less effective for preparing biphosphine ligands having a substituted alkylene group —X—.

It would be desirable to have effective processes for preparing a biphosphine ligand (I) without loss of R groups, and more desirable still if some of the further disadvantages associated with the two prior art methods described above could be overcome, in whole or even in part.

It would also be desirable to have an improved process for manufacturing a compound $R_3P$, for those routes which will still require such an intermediate.

We have now devised processes which utilize a compound of the general formula $R_2P$-L (IV) where L is a leaving group. Aspects of the invention set out hereinafter relate to the use of a compound $R_2P$-L in processes leading to a biphosphine ligand (I); and to the preparation of a compound $R_2P$-L via a compound R—Li, which itself may be prepared by a novel process which constitutes a further aspect of the invention. Furthermore we have devised an improved process for preparing a compound $R_3P$, which improved process may advantageously proceed via the compound R—Li prepared by the said novel process therefor.

In describing these processes in more detail we shall frequently use the variables R, X, L and Hal, already introduced, and variables Q, $E^1$, $E^2$, z, $R^1$ and $R^2$ to be described hereinafter. Such variables may be as defined in any of the broad definitions or subsidiary definitions applying to them given anywhere herein unless we expressly indicate otherwise, for example by stating that a definition is given for a particular compound or process described.

We shall now describe the various aspects of the present invention, leading to the formation of a compound $R^1{}_2P$-L (IV), where $R^1$ is as hereinafter defined.

The first such aspect relates to the preparation of a compound $R^1$—Li. In this aspect (and other aspects which refer to $R^1$ and not to R), $R^1$ is an aryl group which is substituted by a substituent which promotes lithiation at the position ortho thereto. Thus, $R^1$ is preferably aryl, especially phenyl, group which is substituted by alkoxy, aryloxy, dialkylamino, dialkylaminoalkyl, dialkylamido, alkoxyalkoxy, alkylthio, alkylsulfonyl(—$SO_2R^a$), dialkylamidosulfonyl (—$SO_2NR^a{}_2$), alkylsulfonate(—$SO_2OR^a$), sulfonate (—$SO_3M$, with M being Li, Na, K or H) or a lithiated hydroxyl group (—OLi). A preferred substituent in all cases is an alkoxy group, especially methoxy, or an aryloxy group, especially phenyloxy. Preferably the group $R^1$ is mono-substituted.

A conventional route to such a compound R1-Li is via a compound R1-Br and n-butyllithium. However, it is an expensive process, at least when the starting compound is the preferred compound, 2-bromoanisole.

It would be desirable to prepare the desired compound R1-Li by direct lithiation of the corresponding compound $R^1$—H. Such processes are in general known, and are suitable for laboratory procedures, but are not well suited to larger scale procedures, for a number of reasons. Firstly lithiation is slow in the hydrocarbon solvents proposed heretofore, for example hexane; even at elevated temperatures the reaction time needed may be days. Secondly, in ethereal solvents proposed heretofore, for example diethyl ether and tetrahydrofuran (THF), the reaction rates are higher (for example typically 50% conversion after 24 hours in diethyl ether at ambient-13-temperature), but high reaction temperatures are generally precluded because of the reactivity of n-butyllithium, towards ethers and, in the case of diethyl ether, its low boiling point. Further, aqueous work up is complicated in the case of THF which in any case has been reported as yielding undesired side-products (Methoden der Organischen Chemie (Houben-Weyl), 4 Auflage, Band XIII/1. Georg Thieme Verlag, Stuttgart, 1970, pp 14–20). In tests we have conducted we have also found that this appears to be correct. Thirdly, whilst modifiers such as N,N,N',N'-tetramethylethylenediamine (TMEDA) have been proposed to increase the rate of lithiation, they are generally used in a 1:1 molar ratio on n-butyllithium, and often demand large amounts of water and/or other solvents for their removal from the final product.

In accordance with a first aspect of the present invention there is provided a process for the lithiation of a compound of general formula $$R^1\text{—H} \qquad (V)$$

wherein $R^1$ is as defined above, with a compound of general formula $$Q\text{-Li} \qquad (VI)$$

where Q represents an alkyl, cycloalkyl, aralkyl or aryl group, the process being carried out in a solvent which comprises an ether compound of general formula $$E^1\text{-O-}E^2 \qquad (VII)$$

where each of $E^1$ and $E^2$ independently represents an optionally substituted alkyl group or an optionally substituted aryl group, and having a boiling point of at least 40° C. at atmospheric pressure.

Suitably the process is carried out at an elevated temperature, and preferably in the range 40° C. to the reflux temperature of the system. More preferably the process is carried out under reflux.

In the context of this patent document the term "atmospheric pressure" is deemed to be a pressure of 76 cm Hg. Reflux temperatures are deemed to be measured at atmospheric pressure.

Suitably in the compound Q-Li the symbol Q represents a $C_{1-8}$ alkyl group (preferably straight chain) or a $C_{3-8}$ cycloalkyl group, for example methyl, n-hexyl, cyclohexyl or, especially, n-butyl. The compound Q-Li is typically obtained from commercial suppliers in a carrier solvent which is not of the formula $E^1$-O-$E^2$. The carrier solvent is typically an alkane or cycloalkane, for example a $C_{4-12}$ alkane or $C_{3-8}$ cycloalkane, of which hexane is most common. Thus, the lithiation reaction is suitably carried out in a co-solvent comprising the compound $E^1$-O-$E^2$ and the carrier solvent in which the compound Q-Li is supplied.

Suitably in the compound $E^1$-O-$E^2$, the symbol $E^1$ represents an optionally substituted alkyl or optionally substituted aryl group and $E^2$ represents an optionally substituted alkyl group. $E^1$ as an optionally substituted aryl group is suitably a group conforming to the definitions given previously for R.

Suitably in the compound $E^1$-O-$E^2$ an optionally substituted alkyl group is an optionally substituted $C_{1-12}$ alkyl group, preferably an optionally substituted $C_{1-6}$ alkyl group, and an optionally substituted aryl group is an optionally substituted phenyl group. A preferred optional substituent of an alkyl group is an alkoxy group, suitably a $C_{1-4}$ alkoxy group, which itself may be substituted by a $C_{1-4}$ alkoxy group. Especially preferred however is an unsubstituted alkyl group. A preferred substituent of an aryl group is an alkoxy or alkyl group, suitably having 1–4 carbon atoms. A substituted aryl group suitably has 1–3 substituents. Especially preferred, however, is an unsubstituted aryl, especially phenyl, group.

Examples of suitable compounds $E^1$-O-$E^2$ include methyl-t-butylether (MTBE), ethyl t-butylether, dibutylether, diisopropylether, butylethylether, dipropylether, 1,2-dimethoxyethane, 1,2-methoxypropane, diglyme and anisole.

An especially preferred compound $E^1$-O-$E^2$ has a boiling point not exceeding 100° C. at atmospheric pressure. Thus, especially preferred solvents from the preceding list are methyl t-butylether (MTBE), ethyl t-butylether, diisopropylether, butylethylether, dipropylether, 1,2-dimethoxyethane and 1,2-methoxypropane.

It should be noted that $E^1$ and $E^2$ cannot both be a $C_{1-2}$ alkyl group (for example $E^1$-O-$E^2$ being diethylether) because of the requirement that the boiling point of the solvent be at least 40° C. at atmospheric pressure.

Most preferably $E^1$ represents a $C_{3-8}$ alkyl group or a phenyl group, especially a branched $C_{3-6}$ alkyl group, and $E^2$ represents a $C_{1-4}$, especially $C_{1-2}$, alkyl group, especially ethyl or methyl. An especially preferred compound of formula $E^1$-O-$E^2$ is methyl t-butylether (MTBE).

An especially preferred compound $R^1$—H is anisole, whilst the compound $E^1$-O-$E^2$ may be anisole. In this case and other cases where $E^1$ is an optionally substituted aryl group or an optionally substituted $C_{1-12}$ alkyl group and $E^2$ is an optionally substituted $C_{1-12}$ alkyl group it is quite feasible for the compound $R^1$—H to function also as the compound $E^1$-O-$E^2$, with appropriate adjustment of quantity, and there is no requirement for such a compound $E^1$-O-$E^2$ to be a compound distinct from the compound $R^1$—H. Thus, the compound of formula $E^1$-O-$E^2$ should either, under the selected reaction conditions, be inert to the lithiation compound Q-Li or if not inert to it, should provide the reactant $R^1$—H.

In the former case the ratio by volume of the compound $E^1$-O-$E^2$ to the said carrier solvent is suitably 1:10–10:1, preferably 1:3–3:1, more preferably 1:2–2:1. As a practical matter, however, in the former case the volume of said carrier solvent will usually be not less than the volume of the compound $E^1$-O-$E^2$. In the latter case the ratio may likewise suitably be 1:10–10:1, but is preferably 1:2–4:1, more preferably 2:3–2:1, by volume of the compound $E^1$-O-$E^2$ (including the reactant $R^1$—H) to the carrier solvent.

We find that when a compound $E^1$-O-$E^2$ is present as the solvent or as a co-solvent a good rate of reaction can be achieved without the need for accelerators such as TMEDA, as proposed in the literature, for example by L. Brandsmaet al. Synthetic Communications, 20(15), pp. 2273–2274,1990. Without an accelerator present the process is preferably carried out for at least 8 hours, preferably for at least 12 hours, but suitably for less than 30 hours, preferably for less than 24 hours. However we do not exclude the use of an accelerator. When an accelerator is used the process is suitably carried out for at least 1 hour, preferably for at least 2 hours, and suitably for less than 12 hours, preferably for less than 10 hours. We find that small amounts of TMEDA may be used, and give effective acceleration. When TMEDA is used it is preferably used in a molar ratio of 0.01–0.5, more preferably 0.02-0.2, relative to the compound Q-Li.

Preferably the molar ratio of the compound $R^1$—H to the compound Q-Li (including in processes in which the reactant $R^1$—Li provides the compound $E^1$-O-$E^2$) is in the range 0.8–6 to 1, preferably 0.8–3 to 1, more preferably, 1–2 to 1. Most preferably it is in the range 1.1–1.6 to 1; especially 1.1–1.3 to 1. In preferred processes the compound $R^1$—H is provided in molar excess over the compound Q-Li and it is found that this gives a good rate of reaction and that all of the lithium reactant can be consumed, leading to clean work-up and/or facilitating the carrying out of subsequent process steps without prior work-up being needed. The good rate of reaction is surprising, since the literature of which we are aware suggests the benefits of using an excess of the lithium compound in achieving faster reaction rates (for example in the process for the lithiation of anisole as described by D. W. Slocum et al, Tetrahedron Letters, Vol. 35, No. 3, pp. 385–388, 1994).

An important phosphorus-containing intermediate is a compound of general formula $$R^1_3P \quad (II)$$

where $R^1$ is as defined above. The compound $R^1_3P$ may be prepared by reaction of a compound $R^1$—Li with $PCl_3$. We have found that the lithiation process of the first aspect facilitates reaction of the resultant compound $R^1$—Li with $PCl_3$. A solvent of the same type as defined above for the first aspect is suitable. The $PCl_3$ to be used may be supplied in a suitable solvent compatible with the compound $E^1$-O-$E^2$ and inert towards the compound R1-Li or may be supplied in the same solvent. The reaction with $PCl_3$ may be carried out without work-up of the reaction mixture from the first aspect. Suitably, the subsequent step of forming the compound $R_3P$ is carried out at a temperature in the range −10 to 50° C., preferably 0 to 40° C., especially 10 to 30° C. External cooling is employed or the temperature kept beneath the selected upper limit by controlling the rate of addition of one reactant to the other. The above conditions may be novel and if so may constitute a further aspect of the invention.

In accordance with a second aspect of the present invention there is provided a process for the preparation of a compound of general formula $$R^1_3P \quad (II)$$

starting with a compound of general formula $$R^1\text{---}H \quad (V)$$

by the two process steps defined above, where $R^1$ is as defined above. Preferably the process of the second aspect is a one-pot process carried out without isolation of the lithiated intermediate $R^1$—Li.

A preferred compound prepared by the process of the second aspect defined above is tris(2-anisyl)phosphine (TOMPP) and this has been found to be prepared in high yield and very high purity, by the process of the second aspect.

Another phosphorus-containing intermediate of value to prepare is a compound of general formula $$R^1_2\text{P-L} \quad (IV)$$

where $R^1$ as defined above and L is a leaving group. Suitably L is an amine, alkoxy, aryloxy, alkylthio or phosphine leaving group —PR"2 where R" is as defined below. Preferred leaving groups L are of formula —NR"2 or -ZR", where R" is an optionally substituted alkyl, aryl, aralkyl or cycloalkyl group, and Z is an oxygen or sulphur atom. In the case of an amine leaving group the two groups R" may be different but are preferably identical. Furthermore in the case of leaving groups —PR"$_2$ and —NR"2 the groups R"$_2$ may together form an optionally substituted alkylene chain, preferably an optionally substituted $C_{4-8}$ alkylene chain, thereby forming, with the hetero atom, a ring structure. In relation to any of these leaving groups L, suitably R" is a $C_{1-6}$ alkyl group, linear or branched, preferably a $C_{1-4}$ alkyl group, more preferably a $C_{1-2}$ alkyl group. Ethyl is an especially preferred group R". Z is preferably an oxygen atom.

A compound $R^1_2$P-L may be prepared by reaction of an organometallic compound containing the group $R^1$ with a compound of general formula $$Hal_2\text{P-L} \quad (VIII)$$

where Hal represents a halogen atom, suitably chlorine, bromine or iodine, preferably chlorine. The organometallic compound may suitably (especially when L is a leaving group —NR"2) be a compound of formula R—Li and in such cases is preferably prepared by a process of the first aspect. Alternatively it may suitably (especially when L is a leaving group -ZR") be a Grignard reagent.

Processes are generally known for reaction of a compound $R^1$—Li with a compound $Hal_2$P-L but do not achieve good yield of the target compound, with high purity. For example in a paper by W. E. McEwen and B. D. Beaver, Phosphorus and Sulfur, 1985, Vol. 24, pp. 259–271 the reported yield of the compound N,N-diethylamino-bis-(2-anisyl)phosphine produced by such a method carried out at room temperature in a solvent comprising hexane and TMEDA is 50%.

In accordance with a third aspect of the present invention there is provided a process for the preparation of a compound of general formula $$R^1_2\text{P-L} \quad (IV)$$

by reaction of a compound of general formula $R^1$—Li (III)s with a compound of general formula $$Hal_2\text{P-L} \quad (VIII)$$

the reaction taking place in a solvent which comprises another compound of general formula $$E^1\text{-O-}E^2 \quad (VII)$$

as defined above, where $R^1$, L, Hal, $E^1$ and $E^2$ are as defined in any of the above definitions.

It is found that when the process of the third aspect employs a solvent comprising the defined ether compound VII the yield is high and the target compound $R^1_2$P-L is obtained in highly pure form.

Suitably the process of the third aspect is carried out at a temperature not exceeding 55° C., preferably not exceeding 50° C., most preferably not exceeding 40° C., and especially not exceeding 30° C. Suitably the process is carried out at a temperature of at least −50° C. More specifically, when the leaving group L is a group —NR"$_2$ the process is suitably carried out at a temperature of at least −30° C., preferably at least —15° C., most preferably at least 0° C. Cooling is generally required for such a process, whereby the temperature of the reaction mixture is preferably between 0 and 25° C. When the leaving group L is a group -ZR" the reaction mixture is preferably kept at −10° C. or below, more preferably at −30° C. or below.

Preferably in the process of the third aspect of the invention L represents an amine leaving group —NR"$_2$. Definitions of preferred amine leaving groups given previously apply.

One suitable way of accessing the compounds of formula IV wherein L represents a group -ZR" is via a corresponding compound of formula IV wherein L represents a group —NR"$_2$, reacted with a compound of formula HZR". Generally a temperature in the range 10–80° C. is suitable and no additional solvent is needed.

An identical compound $E^1$-O-$E^2$ may be employed in the first and third aspects of the invention. The process of the third aspect may be carried out without work-up of the reaction mixture from the first aspect.

In accordance with a fourth aspect of the invention there is provided a process for the preparation of a compound of general formula

$R^1{}_2$P-L     (IV)

starting with a compound of general formula

$R^1$—H     (V)

by a process of the first aspect followed by a process of the third aspect, with $R^1$ and L are as defined in any of the above definitions. Preferably, the process of the fourth aspect is a one-pot process carried out without isolation of the lithiated intermediate $R^1$—Li.

Preferably the compound of formula $R^1{}_2$P-L is isolated at the end of the process of the third or fourth aspect. This may be achieved by standard work-up methods.

An alternative route to a compound of formula $R^1{}_2$P-L is by preparation of the Grignard reagent $R^1$—Mg-Hal, where Hal is a halogen atom, for example chlorine, bromine or iodine, followed by reaction with a said compound Hal$_2$P-L. Tetrahydrofuran is a suitable solvent for both steps. The formation of the Grignard reagent suitably takes place under standard conditions. The second step of reacting the Grignard reagent suitably takes place at a depressed temperature, for example −30° C. to 20° C.

The compounds Hal$_2$P-L required for processes described above are commercially available and/or may be prepared by standard methods. Compounds Hal$_2$P—NR"2 and Hal$_2$P-ZR" maybe prepared by the well-known reactions of the compounds HNR"$_2$ and HZR" respectively with PHal$_3$ (conveniently PCl$_3$), for example in diethyl ether at a temperature in the range −20° C. to 40° C. The compounds Cl$_2$P—OEt and Cl$_2$P—NEt$_2$ are commercially available.

Next we describe onward reactions of a compound R$_2$P-L (IV) to yield a compound R$_2$P—X—PR$_2$ (I) where R, L and X are as defined in any of the above definitions, and intermediate compounds thereto. It should be noted that the group R may be as most broadly defined above, since the compound R$_2$P-L may not necessarily have been prepared in accordance with the third or fourth aspects as defined above, in which the restricted definition $R^1$ applies. Methods for the preparation of further compounds R$_2$P-L are within the knowledge of the person skilled in the art but suitable methods are also described in the examples which follow.

In one onward reaction it is desired to form an intermediate compound of general formula

R$_2$P-M     (IX)

where R is as defined in any of the above definitions and M represents an alkali metal atom.

In the textbook Neuere Methoden der Praparativen Organischen Chemie, Band II, Verlag Chemie 1960, pp. 133,140, it is mentioned that dialkylamino-dialkylphosphines can be cleaved with sodium. It is stated that (n-Bu)$_2$P—NEt$_2$ is cleaved with sodium in toluene in 53% yield. However when we attempted to repeat this reaction we found that no reaction took place.

In the article entitled Aspects of the Cleavage of Phosphines with Potassium: Synthesis and Reactivity of Lithium and Potassium Bis (p-(dimethyl-amino)phenyl)-phosphide by Toth et al, in Organometallics, 1980, pp. 675–680, it is stated that the compound is Et$_2$NP(P—C$_6$H$_4$NMe$_2$)$_2$ was recovered unchanged after attempts to cleave it with sodium and potassium.

In Japanese patent application 47-47014 of Saitama University there is disclosed a process in which an alkyldiphenylphosphinite, for example ethyldiphenylphosphinite or methyldiphenylphosphinite, is reacted with sodium or potassium in an inert solvent under reflux conditions to yield the compound Ph$_2$P—Na or Ph$_2$P—K, and that compound reacted with a dichloroalkane Cl(CH$_2$)$_m$Cl (where m is from 1 to 5) to yield a final compound Ph$_2$P(CH$_2$)$_m$PPh$_2$. In the examples yields of the final compound, calculated on the basis of the phosphinite, are 94% (Example 1 using sodium), 30% (Example 2 using potassium), and 63% (Example 3 using sodium). For Example 1 which produced the highest yield the time allowed for the first step was 35 hours.

In accordance with a fifth aspect of the present invention there is provided a process for the preparation of a compound of general formula

R$_2$P-M     (IX)

by reaction of a compound of formula

R$_2$P-L     (IV)

with an alkali metal M, where R and L are as defined in any of the above definitions, but excluding a process in which the compound R$_2$P-L is an alkyldiphenylphosphinite and in which the compound R$_2$P-M is Ph$_2$P—Na or Ph$_2$P—K.

In accordance with a sixth aspect of the present invention there is provided a process for the preparation of a compound of general formula

R$_2$P-M     (IX)

by reaction of a compound of formula

R$_2$P-L     (IV)

with an alkali metal M, where R and L are as defined in any of the above definitions, at a temperature not exceeding 60° C.

In accordance with a seventh aspect of the present invention there is provided a process for the preparation of a compound of general formula

R$_2$P-M     (IX)

by reaction of a compound of formula

$$R_2P\text{-}L \qquad (IV)$$

with an alkali metal M, where R is as defined above and L is an amine leaving group as defined above.

In accordance with an eighth aspect of the present invention there is provided a process for the preparation of a compound of general formula

$$R_2P\text{-}M \qquad (IX)$$

by reaction of a compound of formula

$$R_2P\text{-}L \qquad (IV)$$

with an alkali metal M, where R and L are as defined in any of the above definitions, wherein the alkali metal M is lithium.

Preferably the process of the fifth, seventh or eighth aspects is carried out at a temperature not exceeding 60° C. Preferably the process of the fifth, sixth, seventh or eighth aspects is carried out at a temperature not exceeding 50° C. In preferred processes of the fifth, sixth, seventh or eighth aspects the reaction temperature is suitably in the range −20° C. to 40° C., preferably −10 to 30° C., especially 0 to 20° C.

In relation to the fifth, sixth and seventh aspects preferably M represents lithium. Whilst sodium and potassium may be employed with reasonable effect we have found lithium to be significantly and unexpectedly advantageous. We have found it to give good yield of the target compound in shorter time than is required for processes employing sodium, to be effective at lower temperatures than are required for processes employing sodium, and to give products of particularly high purity, possibly as a consequence of the shorter time and lower temperature required. We have also found that a lower temperature than suggested by JP 47-47014 can be employed, including when sodium is used.

In relation to the fifth, sixth and eighth aspects, a preferred leaving group L is an amine leaving group —NR''$_2$, as previously defined.

When L is an amine leaving group it is preferred that groups $R^1$, as previously defined, are employed.

In relation to the fifth, sixth and eighth aspects, another preferred leaving group is a leaving group -ZR'', as previously defined, and it is then preferred that a group R is an optionally substituted alkyl or optionally substituted aryl group, as previously defined; but the latter are most preferred.

Preferably the alkali metal employed in the process of the fifth, sixth, seventh or eighth aspect is in the form of a dispersion in a suitable carrier, typically a mineral oil. When mixed with the compound R$_2$P-L this has been found to give a better rate of reaction than the use of the alkali metal in a granular or particulate form.

Preferably the process of the fifth, sixth, seventh or eighth aspect is carried out in a suitable organic solvent, which does not react with the alkali metal employed and which does not protonate the R$_2$P— anions. Suitable solvents include aromatic hydrocarbon solvents, for example benzene optionally substituted by 1 to 3 C$_{1-4}$ alkyl groups, for example benzene and toluene; ethers, for example di(Cl-4 alkyl)ether and diglyme, and cyclic ethers such as tetrahydrofuran and dioxane; and ammoniacal solvents, for example liquid ammonia.

We have found that certain reactions, especially those in which M is sodium, may be accelerated by the presence of naphthalene. Small amounts of naphthalene in a larger amount of another solvent, for example one of the other solvents mentioned above, may be sufficient to bring about a substantial improvement, to the extent where a process employing sodium or potassium becomes a useful one even at low or moderate temperature. The molar ratio of the alkali metal M, suitably potassium or, especially sodium, to naphthalene, may be in the range 3–30 to 1, preferably 5–20 to 1. The presence of naphthalene may also assist a process of the fifth, sixth, seventh or eighth aspect in which the alkali metal is lithium but since lithium appears to be inherently more effective than sodium in the processes described and preferred processes in which the alkali metal is lithium do not employ naphthalene as a reaction accelerator. Diglyme and dioxane are preferred solvents, for reactions in which M is sodium.

If wished the resultant compound R$_2$P-M may be isolated. In some processes of the fifth, sixth, seventh and eighth aspects this may be very straightforward, because of the precipitation of one or other of the compounds R$_2$P-M and M-L.

In some processes a quenching agent may be added. We have found that ammoniacal or amine quenching agents such as acid addition salts of ammonia or amines (for example NH$_4$Cl, and di(C$_{1-4}$ alkyl)NH.HCl) are suitable.

In accordance with a ninth aspect of the present is invention there is provided a process for the preparation of a compound of general formula

$$R^1{}_2P\text{-}M \qquad (IX)$$

starting with a compound of general formula

$$R^1\text{—}Li \qquad (III)$$

by a process of the third aspect, for the preparation of an intermediate of general formula

$$R^1{}_2P\text{-}L \qquad (IV)$$

followed by a process of the fifth, sixth, seventh or eighth aspect, where $R^1$, L and M are as defined in any of the above definitions.

In accordance with a tenth aspect of the present invention there is provided a process for the preparation of a compound of general formula

$$R^1{}_2P\text{-}M \qquad (IX)$$

starting with a compound of general formula

$$R^1\text{—}H \qquad (V)$$

by a process of the fourth aspect to prepare an intermediate of general formula

$$R^1{}_2P\text{-}L \qquad (IV)$$

followed by a process of the fifth, sixth, seventh or eighth aspect, where $R^1$, L and M are as defined in any of the above definitions.

We will now describe the preparation of a compound R$_2$P—X—PR$_2$ (I) from compounds R$_2$P-M and Hal-X-Hal where Hal is a halogen atom and R, X and M are as defined in any of the above definitions. As mentioned above JP-A 47014 discloses the reaction of a compound Ph$_2$P—Na or Ph$_2$P—K with a dichloroalkane Cl(CH$_2$)$_m$Cl where m is 1 to 5.

We have devised significant improvements to this generally known reaction and/or have found this generally known reaction to be applicable to reactants to which it has not heretofore been applied. We outline these findings below.

We have found the reaction to be applicable to compounds of formula $R_2P$-M in which R is other than phenyl. In particular R may be a substituted phenyl group as defined in any of the above definitions, especially a phenyl group bearing an alkoxy substituent, and we have found that the presence of such substituents does not appear to have an adverse effect on the process. Also, we have shown that R may be an optionally substituted alkyl group.

Whilst other alkali metals may be employed we favor the use of a lithiated compound $R_2P$—Li. We find this to be a very effective reactant but also, as described above, to be favored by reason of its ease of preparation.

We have found the process to be applicable to a wide range of bridging groups X, not just to the straight chain methylene bridges disclosed in JP-A 47014. We have not found any limitations on the bridging group X in carrying out this process and regard the broad definitions given previously as being applicable. However we may define preferred bridging group in relation to this aspect as a group containing 2 to 4 bridge carbon atoms bearing 1 to 3 $C_{1-4}$, preferably $C_{1-2}$, alkyl groups; especially a propane bridge which is 2-substituted or 2,2'-disubstituted, the middle carbon atom suitably carrying one $C_{1-4}$ alkyl group or two $C_{1-4}$ alkyl, preferably $C_{1-2}$ alkyl groups; most preferably two identical groups. Especially preferred are propane bridges having 2,2-dimethyl, 2-methyl, 2-n-propyl, 2-n-butyl and 2-ethyl substituents.

Whilst other halogen atoms may be employed we favor the use of a dibromo compound, since such compounds seem more effective than corresponding dichloro compounds in processes for preparing compounds of formula (I) having substituted bridging groups, as defined in the preceding paragraph.

We have found that the presence of a polar aprotic solvent assists the process.

We have found it best to avoid a very long reaction time as used to produce the best yield of a target product in JP-A 47014, Example 1. We suitably allow no more than 15 hours for the reaction, preferably no more than 6 hours, most preferably no more than 3 hours.

We have found that processes in which a polar aprotic solvent is present and which are run for no more than the number of hours stated above, and preferably for no more than three hours, are very "clean", giving high yields with only low amounts of undesired and difficult to remove by-products.

In accordance with an eleventh aspect of the invention, there is provided a process for the preparation of a compound of general formula $$R_2P-X-PR_2 \quad (I)$$

from compounds of general formulae $R_2P$-M (IX) and Hal-X-Hal (X), the process comprising one or more of the features described in the preceding seven paragraphs, R, X, M and Hal being as defined in any of the above definitions. Suitably the compound $R_2P$-M is not $Ph_2P$—Na or $Ph_2P$—K whilst Hal-X-Hal is Cl—$(CH_2)_m$—Cl where m is 1 to 5.

Suitably a process of the eleventh aspect is carried out at a temperature not exceeding 60° C., preferably at a temperature in the range —20° C. to 40° C., more preferably –10° C. to 30° C., especially 0° C. to 20° C.

A process of the eleventh aspect is preferably carried out in the presence of a polar aprotic solvent, for example dimethylsulphoxide (DMSO). Alternatively a solvent mentioned above as being suitable for the fifth, sixth, seventh or eighth aspect may be present. In a preferred process of the eleventh aspect solvents according to both such definitions are used in admixture, as co-solvents.

In accordance with an twelfth aspect of the present invention there is provided a process for the preparation of a compound of general formula $$R_2P-X-PR_2 \quad (I)$$

starting with a compound of the general formula $$R_2P-L \quad (IV)$$

where R, X and L are as defined in any of the above definitions by a process of the fifth, sixth, seventh or eighth aspect of the present invention and a process of the eleventh aspect.

Preferably, the process of the twelfth aspect is a one-pot process carried out without isolation of the intermediate compound of formula $R_2P$-M- Preferably a polar aprotic solvent is added to the reaction mixture at an intermediate stage of the process (that is, once it is required to react the compound $R_2P$-M with the compound Hal-X-Hal). Optionally no quench step is carried out at the intermediate stage of the process.

In accordance with a thirteenth aspect of the present invention there is provided a process for the preparation of a compound of general formula $$R^1_2P-X-PR^1_2 \quad (I)$$

starting with a compound of general formula $$R^1-Li \quad (III)$$

where $R^1$ and X are as defined in any of the above definitions, by a process of the third aspect followed by a process of the twelfth aspect.

In accordance with a fourteenth aspect of the present invention there is provided a process for the preparation of a compound of general formula $$R^1_2P-X-PR^1_2 \quad (I)$$

starting with a compound of general formula $$R^1-H \quad (V)$$

where $R^1$, X and L are as defined in any of the above definitions, by a process of the fourth aspect followed by a process of the twelfth aspect.

In another onward reaction a compound $R_2P$-L (IV) is reacted with a compound Hal-X-Hal (X) where R, Hal and X are as defined in any of the above definitions and L is an amine leaving group —NR"2 when R" is as defined in any of the above definitions and the resultant compound is treated with a reducing agent to yield a compound $R_2P$—X—$PR_2$(I). The product of the reaction between compounds (IV) and X is believed to be a phosphonium salt of general formula $$R_2P^+(L)\text{-}X\text{—}P^+(L)R_2 \text{ 2Hal-} \quad (XI)$$

In accordance with a fifteenth aspect of the present invention there is provided a process for the preparation of a compound of general formula $$R_2P^+(L)\text{-}X\text{—}P^+(L)R_2 \text{ 2Hal-} \quad (XI)$$

where R, X and Hal are as defined in any of the above definitions and L is an amine leaving group —NR"2 as defined in any of the above definitions, by reaction of a compound of general formula $$R_2P-L \quad (IV)$$

with a compound of general formula

Hal-X-Hal (X)

Preferably the process is carried out in an organic solvent, preferably comprising a polar aprotic solvent. Examples are diethylacetamide and acetonitrile. Acetonitrile is a preferred solvent.

Suitably the process of the fifteenth aspect is carried out at an elevated temperature, preferably at a temperature of at least 40° C., more preferably at least 60° C. The reaction is preferably carried out under reflux.

Preferably the moiety —X— in the compound of formula X used in the process of the fifteenth aspect of the present invention is a $C_{2-4}$ alkylene group optionally substituted by one $C_{1-4}$ alkyl group. Preferably it is a 2-($C_{1-4}$ alkyl)propane group or, especially, a propane group. Each moiety Hal is preferably a bromine atom.

Preferably a moiety R in the compound of formula IV used in the fifteenth aspect is an optionally substituted alkyl group or an optionally substituted aryl group, as defined in any of the above definitions.

In accordance with a sixteenth aspect of the present invention there is provided a process for the preparation of a compound of general formula $$R_2P^+(L)\text{-}X\text{—}P^+(L)R_2 \; 2Hal\text{-} \quad (XI)$$

starting with a compound of general formula $$R^1\text{—}Li \quad (III)$$

where $R^1$, L, X and Hal are as stated for the fifteenth aspect, by a process of the third aspect followed by a process of the fifteenth aspect.

In accordance with a seventeenth aspect of the present invention there is provided a process for the preparation of a compound of general formula $$R_2P^+(L)\text{-}X\text{—}P^+(L)R_2 \; 2Hal\text{-} \quad (XI)$$

starting with a compound of general formula $$R^1\text{—}H \quad (V)$$

where $R^1$, X, Hal and L are as stated for the fifteenth aspect, by a process-of the fourth aspect followed by a process of the fifteenth aspect.

In accordance with an eighteenth aspect of the present invention there is provided a compound having a cation of general formula $R_2P^+(L)\text{-}X\text{—}P^+(L)R_2$ (XII), moieties R, X and L being as stated for the fifteenth aspect.

Since we believe cations of formula (XII) to be novel we are not aware of any precedent for their reduction to compounds $R_2P\text{—}X\text{—}PR_2$. We have found however that methods of the type proposed for reduction of cations $R_3P^+\text{—}X\text{—}P^+R_3$, for example in EP-A-364046, are suitable for reduction of such cations of formula $R_2P^+(L)\text{-}X\text{—}P^+(L)R_2$, and for a wide range of such compounds, in terms of variability of groups R. It is surprising that a group L is removed so selectively in preference to a group R, given that at least certain groups R would normally also be regarded as good leaving groups, for example preferred group 2-anisyl. Indeed, in the process of EP-A-364046 it is a group R, preferably a 2-anisyl group, which is the leaving group. Linked with this is the fundamental advantage that loss of the amine leaving groups L hereof is inexpensive whereas loss of leaving groups R, in particular 2-anisyl groups, is expensive having regard to the need to prepare at least a 50% excess of the lithiated starting compound, in particular 2-lithioanisole.

In accordance with an nineteenth aspect of the present invention there is provided a process for the preparation of a compound of general formula $$R_2P\text{—}X\text{—}PR_2 \quad (I)$$

by reduction of a cation of general formula $$R_2P^+(L)\text{-}X\text{—}P^+(L)R_2 \quad (XII)$$

where R, L, X and Hal are as stated for the fifteenth aspect.

Preferably the reduction is achieved by use of a reducing agent. A suitable reducing agent is an alkali metal aluminium tetrahydride or a compound which may be considered as derived therefrom by replacing one, two or three of its hydrogen atoms with the same or different groups —$OR_2$ where $R_2$ is an alkyl group, preferably a $C_{1-4}$ alkyl group, especially a $C_{1-2}$ alkyl group, or where $R_2$ is an alkoxyalkyl group, preferably a $C_{1-4}$ alkoxy ($C_{1-4}$ alkyl) group, more preferably a ($C_{1-2}$ alkoxy)($C_{1-2}$ alkyl) group, especially a 2-methoxyethyl group. Alkoxyalkyl groups are preferred groups $R_2$. A preferred reducing agent is an alkali metal tetrahydride or a compound which may be considered as derived therefrom by replacing two of its hydrogen atoms with identical groups —$OR_2$. $R_2$ preferably being an alkoxyalkyl group. Preferred reducing agents are lithium aluminium tetrahydride and, especially, sodium bis(2-methoxyethyloxy) aluminium dihydride.

Suitably the process of the nineteenth aspect is carried out in an aprotic organic solvent, which may be polar or non-polar. Admixed polar and non-polar solvent may be employed. Examples of suitable polar aprotic solvents include tetrahydrofuran, the dimethyl ether of ethyleneglycol (mono-glyme) and the dimethyl ether of diethylene glycol (diglyme). Examples of suitable aprotic non-polar solvents are aromatic compounds having 1–3 $C_{1-4}$ alkyl groups, for example benzene and toluene. Non-polar aprotic solvents are preferred.

The process of the nineteenth aspect is preferably carried out at a temperature not exceeding 120° C., preferably at a temperature not exceeding 60° C., most preferably at a temperature not exceeding 50° C. A preferred temperature for the process is in the range 10 to 40° C.

In accordance with an twentieth aspect of the present invention there is provided a process for the preparation of a compound of general formula $$R_2P\text{—}X\text{—}PR_2 \quad (I)$$

starting with a compound of general formula $$R_2P\text{-}L \quad (IV)$$

where R. X and L are as stated for the fifteenth aspect, by a process of the fifteenth aspect followed by a process of the nineteenth aspect.

In accordance with a twenty-first aspect of the present invention there is provided a process for the preparation of a compound of general formula $$R^1{}_2P\text{—}X\text{—}PR^1{}_2 \quad (I)$$

starting with a compound of general formula $$R^1\text{—}Li \quad (III)$$

by a process of the third aspect to prepare an intermediate of general formula $$R^1{}_2P\text{-}L \quad (IV)$$

where $R^1$, Z, X and L are as stated for the fifteenth aspect, followed by a process of the twentieth aspect.

In accordance with a twenty-second aspect of the present invention there is provided a process for the preparation of a compound of general formula $$R^1{}_2P\text{—}X\text{—}PR^1{}_2 \quad (I)$$

starting with a compound of general formula $$R^1\text{—}H \quad (V)$$

by a process of the fourth aspect to prepare an intermediate of general formula $$R^1{}_2P\text{-}L \quad (IV)$$

where $R^1$, X and L are as stated for the fifteenth aspect, followed by a process of the twentieth aspect.

In accordance with a twenty-third aspect of the present invention there is provided a product prepared by any process defined above as being an aspect of the present invention.

In accordance with a twenty-fourth aspect of the present invention there is provided a catalyst composition of the type defined in any of the above definitions, wherein the phosphine ligand is of general formula $$R_2P\text{—}X\text{—}PR_2 \text{ or } R^1{}_2P\text{—}X\text{—}PR^1{}_2 \quad (I)$$

where R, $R^1$ and X are as defined in any of the above definitions and is prepared by a process of the eleventh, twelfth, thirteenth, fourteenth, nineteenth, twentieth, twenty-first of twenty-second aspects.

In accordance with a twenty-fifth aspect of the present invention there is provided a polymerization process of the type defined in any of the above definitions, wherein the catalyst composition is of the twenty-fourth aspect.

In accordance with a twenty-sixth aspect there is provided a copolymer of the type defined in any of the above definitions, prepared by the process of the twenty-fifth aspect.

In relation to any process defined herein employing or preparing a compound having two or more groups R, $R^1$ or $R^2$, such groups may be different within the compound but are preferably the same.

The invention will now be illustrated by means of the following examples.

Unless otherwise stated, all reactions and manipulations were conducted under an appropriate inert atmosphere (argon for processes using lithium); all reactions were carried out under anhydrous conditions; all solvents were dried and degassed; and all glassware was dried overnight at 150° C.

EXAMPLE 1

Preparation of 2-lithioanisole then tri(2-anisyl) phosphine (TOMPP)

A 2 liter reaction vessel, equipped with a thermometer, a mechanical stirrer, a dropping funnel and a reflux condenser was connected to a supply of inert gas and charged with 113 g (1.04 moles) of anisole and 250 ml of MTBE (methyl tert-butylether). After degassing, 440 ml(0.70 moles) of n-butyllithium (1.6 M in hexane) was added over a 1 hour period, during which the temperature was gradually raised to reflux temperature (about 60° C.). After being kept for 16 hours at this temperature, the reactor contents were cooled to ambient temperature (at this point GC analysis showed >99% conversion of n-butyl-lithium and formation of the corresponding amount of 2-lithioanisole). Next, a mixture of 100 ml of MTBE and 19.3 ml (31.0 g, 0.225 mol) of phosphorus trichloride was added at such a rate that the temperature of the reaction mixture did not exceed 30° C. After the addition was complete the white/yellow suspension was stirred for another 4 hours. Subsequently, 30 ml of water were added and the white precipitate was filtered off. Next, the white solid was washed with methanol (2×200 ml), filtered, and dried under vacuum (1 mbar, 60° C.). Yield: 63.4 g (80%) of a fine white powder, which is >99% pure TOMPP according to $^1$H NMR and $^{31}$P NMR.

EXAMPLE 2

Preparation of 2-lithioanisole then tri(2-anisyl) phosphine (TOMPP)

A 2 liter reaction vessel, equipped with a thermometer, a mechanical stirrer, a dropping funnel and a reflux condenser was connected to a supply of inert gas and charged with 76 g (0.84 moles) of anisole, 8.1 g (0.07 mol) of TMEDA and 250 ml of MTBE-(methyl tert-butylether). After degassing, 440 ml (0.70 moles) of n-butyllithium (1.6 M in hexane) was added over a 1 hour period. After addition was complete the temperature was raised to reflux temperature (about 60° C.). After being kept for 8 hours at this temperature, the reactor contents were cooled to ambient temperature (at this point GC analysis showed >99% conversion of n-butyllithium and formation of the corresponding amount of 2-lithioanisole). Next, a mixture of 100 ml of MTBE and 19.3 ml (31.0 g,0.225 mol) of phosphorus trichloride was added at such a rate that the internal temperature did not exceed 30° C. After the addition was complete the white/yellow suspension was stirred for another 4 hours. Subsequently, 30 ml of water was added and the white precipitate was filtered off. Next, the white solid was washed with methanol (2×200 ml), filtered and dried under vacuum (1 mbar, 60° C.). Yield 62 g (78%) of a fine white powder, which is >99% pure TOMPP according to $^1$H NMR and $^{31}$P NMR.

EXAMPLE 3

Comparative: attempted preparation of 2-lithioanisole then tri(2-anisyl)phosphine (TOMPP)

A lithiation reaction in tetrahydrofuran (THF) was attempted according to the method described in Example 12 of WO 97/37765 (BP).

A solution of 8.1 ml of n-butyllithium in hexane (2.5 M; 20 mmol) was added to a degassed solution of 2.16 g anisole (20 mmol) in 25 ml of THF (distilled from sodium) kept under argon at ambient temperature. After addition was complete (20 minutes) the mixture was stirred for 4 hours at ambient temperature. A GC analysis indicated that after two hours full conversion of anisole was not obtained, with some 15% of the anisole and some 5% of n-butyllithium still unconverted. After 4 hours, still 15% of the anisole was unconverted and no n-butyllithium could be detected. We concluded that in this reaction in THF under the conditions stated in WO 97/37765 (BP) full conversion of anisole was not achieved, and that an undesirable butyllithium was consumed by side reaction(s).

EXAMPLE 4

Preparation of 2-lithioanisole

In a similar process to Example 1, also not using TMEDA or another accelerator, anisole was used as solvent and reactant, the ratio of hexane (carrier solvent for then-butyllithium) to anisole being 1:1 v/v. After 20 hours at a temperature of 42° C. the conversion of n-butyllithium was 94% and the selectivity of the conversion to 2-lithioanisole was 90.5%.

EXAMPLE 5

Preparation of 2-lithioanisole

In a process similar to Example 1. also not using TMEDA or another accelerator, the influence of temperature on rate of lithiation of anisole in a solvent system comprising hexane/MTBE (2:1 v/v) was assessed. The results are set out in Table 1 below.

TABLE 1

| Temp (° C.) | Conversion of n-BuLi after 8 hours (%) | Selectivity to 2-lithio-anisole |
|---|---|---|
| 25 | 56 | 98.0 |
| 42 | 82 | 96.9 |
| 55 | 92 | 96.4 |

In Examples 1 to 5 to monitor progress of the lithiation reactions 0.3 ml of trimethylchlorosilane was added to a 1 ml aliquot of the crude reaction mixture. The mixture was homogenized and allowed to stand for 5 minutes. Then, 2 ml of water was added, in the case of MTBE as reaction solvent 1 ml of hexane was added and the sample was analyzed by gas chromatography (CP Sil 5CB column, temperature program 40° C.-4 min/10° C./min/270° C.-3 min). Conversions were calculated from the areas of 1-trimethylsilylbutane, anisole and o-trimethylsilylanisole.

EXAMPLE 6

Preparation of 2-lithioanisole then N,N-diethylamino-bis(2-anisyl)phosphine

A 2 liter reaction vessel, equipped with a thermometer, a mechanical stirrer, a dropping funnel and a reflux condenser was connected to a supply of inert gas and charged with 113 g (1.04 moles) of anisole and 250 ml of MTBE. After degassing, 440 ml (0.7 moles) of n-butyllithium (1.6 M in hexane) were added over a 1 hour period, during which time the temperature was gradually raised to reflux temperature (about 60° C.). After being kept for 16 hours at this temperature, the reaction mixture was cooled to 0° C. Next, a mixture of 150 ml of MTBE and 61.0 g (0.35 mol) of N,N-diethylamino-dichlorophosphine was added at such a rate that the temperature was kept below 25° C. After addition was complete the white/yellow suspension was stirred for another 4 hours at ambient temperature. Subsequently, 800 ml of water were added. The aqueous phase was, extracted with 100 ml of MTBE and the combined organic layers were washed with water (2×100 ml), dried on magnesium sulphate and concentrated in vacuo (1 mbar, 100° C.). The residue was recrystallized from boiling hexane. The desired product was obtained as off-white solid in 88% yield and excellent purity according to $^1$H, $^{13}$C, and $^{31}$P NMR.

EXAMPLE 7

Preparation of 2-bromomagnesium anisole then ethyl bis(2-anisyl)phosphinite

To a 1 liter reaction vessel charged with 10.9 g (0.448 mol) of magnesium turnings and 250 ml of THF, 76.1 g (0.407 mol) of 2-bromoanisole was added at such a rate that a temperature of 60° C. was reached. Upon completion of the addition, the reaction vessel was kept for 2 hours at 60° C. and subsequently cooled to −15° C. Next, a mixture of 29.83 g (0.203 mol) ethyl dichloro-phosphinite and 50 ml of THF was added over a period of 3 hours. After being kept for another 30 min at −15° C., the mixture was stirred at ambient temperature overnight. Then, 44 ml of water containing 4 g of triethylamine were added. More water and toluene were added until a phase separation was observed. The organic phase was separated and the aqueous phase was extracted with toluene (2×100 ml). The combined organic phases were washed with 100 ml of water and concentrated to dryness. The solid residue was washed with some heptane and dried. Yield: 35.9 g (61%) of ethyl bis(2-anisyl) phosphinite ($An_2P$—OEt), which was pure according to $^{31}$P and $^1$H NMR.

EXAMPLE 8

Preparation of N,N-diethylaminodichlorophosphine

A 1 liter reaction vessel equipped with a mechanical stirrer, a 500 ml addition funnel, and a reflux condenser, was charged with 111.7 g (0.8 mol) of $PCl_3$ and 350 ml of hexane. Over a period of 1 hour, 119.0 g (1.6 mol) of diethylamine was slowly added whilst the reaction vessel was kept at 0° C. Upon addition the reaction vessel was stirred for 2 hours at ambient temperature. Next, the yellow reaction mixture was filtered over a P3 glass frit and the residue was washed 3 times with 100 ml of hexane. The combined organic fractions were concentrated on a rotary evaporator and distilled under vacuum (7 mbar, 67° C.). Yield: 120 g (87%) of the title compound as a clear liquid.

EXAMPLE 9

Preparation of di(n-butyl)N,N-diethylaminophosphine

See H. Nöth, H. -J. Vetter, Chem. Ber. 96, pp. 1109–18, 1963

To a solution of 19.4 g (0.112 mol) of $Cl_2PNEt_2$ in 50 ml of diethyl ether, which was cooled to −78° C., were slowly added 139.5 ml (0.22 mol) of a 1.6 M solution of n-butyllithium in hexane. When the addition was completed, the solution was allowed to warm to room temperature and stirred for 1 hour. Next, the solution was concentrated on a rotary evaporator. The resulting suspension was subjected to a vacuum distillation, which yielded 19.1 g of a colorless liquid with a boiling point of 75–76° C. at 0.5 mbar. According to $^1$H and $^{31}$P NMR the liquid was the pure title compound.

EXAMPLE 10

Preparation of di(n-butyl)ethylphosphinite

A mixture of 5.0 g (0.023 mol) of n-$Bu_2PNEt_2$ and 25 ml of dry degassed absolute ethanol was heated for 24 hours at 60° C. At this point analysis of the crude reaction mixture with 31P NMR showed that ~95% of the starting material had been selectively converted into n-$Bu_2POEt$. The volatile components were removed under vacuum (1 mbar) at 30° C. to yield the title compound as a colorless liquid.

EXAMPLE 11

Preparation of diphenyl N,N-diethyl-aminophosphine

To a solution of 25.0 g (0.107 mol) of $Ph_2PCl$ (ex. Aldrich, 95% pure) in 150 ml of diethyl ether, which was cooled to 5–10° C., were added over a period of 1 hour 37.8 ml (0.28 mol) of diethylamine. When the addition was completed, the suspension was allowed to stir overnight at room temperature. Next, the mixture was filtered over a P3 glass frit and the solid residue was washed with 2×50 ml of hexane. The organic fractions was combined, concentrated on a rotary evaporator, and distilled under vacuum to yield 30 g of a clear liquid (boiling point 146–148° C. at 0.1 mbar). According to $^1$H and $^{31}$P NMR the liquid was the pure title compound.

EXAMPLE 12

Preparation of diphenyl ethylphosphinite

A mixture of 5.4 g (0.020 mol) of $Ph_2PNEt_2$ and 25 mls of dry degassed absolute ethanol was heated for 48 hours at 60° C. At this point analysis of the crude reaction mixture with $^{31}$P NMR showed that all starting material had been selectively converted into $Ph_2POEt$. The volatile components were removed under vacuum (1 mbar) at 30° C. to yield the title compound as a colorless liquid.

EXAMPLE 13

Preparation of lithio-bis(2-anisyl)phosphine then 2, 2-diethyl-1,3-bis(bis(2-anisyl)phosphino)propane A 1 liter reaction vessel equipped with a mechanical stirrer and a reflux condenser was charged with 300 ml of dioxane and 16.05 g of a lithium dispersion in mineral oil (containing 4.81 g of lithium metal=0.693 mol). Next, a solution of 100.58 g (0.346 mol) of ethyl bis(2-anisyl)-phosphinite in 250 ml dioxane were added at 12° C. over a period of 4 hours. The mixture was stirred for 16 hours at 12° C. after which time a precipitate had formed and $^{31}$P NMR indicated the full conversion of the starting phosphine and the quantitative formation of $An_2PLi$. Next, 100 ml of DMSO were added followed by slow addition of 40.22 g (0.156 mol) of 1,3-dibromo-2,2-diethylpropane at 12° C. After stirring the reaction mixture overnight, still at 12° C., $^{31}$P NMR indicated the quantitative formation of the title compound. The reaction mixture was worked by adding 20 ml of methanol, followed by removal or 300 ml solvent under vacuum at 50° C., addition of water and 200 ml of dichloromethane followed by phase separation. The aqueous phase was extracted with 2×50 ml of dichloromethane and the combined organic phases were washed with water (2×50 ml) and concentrated to 10% of the original volume. Addition of methanol (200 ml) led to precipitation of the desired product. The product was filtered off, washed with a little methanol, and dried. Yield was 75 g (77%) of a white solid, which is >97% pure by $^{31}$P and $^1$H NMR.

EXAMPLE 14

Preparation of lithio-bis(2-anisyl)phosphine then 2, 2-diethyl-1,3-bis(bis(2-anisyl)phosphino)propane A 100 ml reaction vessel equipped with a mechanical stirrer and a reflux condenser was charged with 2.90 g (10 mmol) of ethyl bis(2-anisyl)phosphinite in 40 ml of dioxane and 0.146 g of lithium granules. The mixture was stirred for 16 hours at 10° C. after which time a precipitate had formed. $^{31}$P NMR indicated the presence of 62 wt % of lithio-bis(2-amisyl)phosphinite and 28 wt % of a tetra-anisyldiphosphine $An_2PPAn_2$. Next 5 ml of DMSO was added followed by slow addition of 0.86 g (3.3 mmol) of 1,3-dibromo-2,2-diethylpropane in 3 ml of THF, still at 10° C. After stirring for another 20 minutes at 10° C., $^{31}$P NMR indicated the presence of 49 wt % of the desired diphosphine, 30 wt % of a tetra-anisyldiphosphine and 16 wt % of 1-bromo-2,2-diethyl-3-bis(2-anisyl)phosphine.

EXAMPLE 15

Preparation of lithio-diphenylphosphine then 2,2-diethyl-1,3-bis(diphenylphosphino)propane A 50 ml reaction vessel equipped with a mechanical stirrer was charged with 1.15 g (5 mmol) of ethyl diphenylphosphinite in 20 ml of dioxane and 280 mg (12.1 mmol) of a 30 wt % lithium dispersion in mineral oil. The mixture was stirred for 2.5 hours during which time a deep red solution was formed. $^{31}$P NMR showed full conversion of the starting phosphine. Lithiodiphenylphosphine was formed almost exclusively. Next, 2.5 ml of DMSO was added followed by slow addition of 0.52 g (2 mmol) of 1,3-dibromo-2,2-diethylpropane in 2.5 ml of THF. After stirring for 1 hour $^{31}$P NMR showed almost exclusively the desired diphosphine. The entire process was carried out at 10° C.

EXAMPLE 16

Preparation of sodium-diphenylphosphine

A 50 ml reaction vessel equipped with a mechanical stirrer and a reflux condenser was charged with 1.15 g (5 mmol) of ethyl diphenylphosphinite in 20 ml of THF, 0.253 g (11 mmol) of small pieces of sodium and 0.128 g (1 mmol) of naphthalene. The reaction mixture was stirred for 20 hours at 10° C. $^{31}$P NMR indicated full conversion of the starting phosphine to sodium diphenylphosphine in 90% selectivity.

EXAMPLE 17

Preparation of lithio-di-n-butylphosphine then 1,3-bis(di-n-butylphosphino)propane A 50 ml reaction vessel equipped with a mechanical stirrer and a reflux condenser was charged with 0.950 g (5 mmol) of ethyl di-n-butylphosphinite in 20 ml of THF and 0.254 g (11 mmol) of a 30 wt % lithium dispersion in mineral oil. The mixture was stirred for 24 hours at 10° C., after which time $^{31}$P NMR indicated full conversion of the starting phosphine. Next, 0.4 g (2 mmol) of 1,3-dibromopropane was added, and the reaction mixture stirred at 10° C. for 1 hour. $^{31}$P NMR showed the desired diphosphine as the main product.

EXAMPLE 18

Preparation of sodium-di-n-butylphosphine

A 50 ml reaction vessel equipped with a mechanical stirrer and a reflux condenser was charged with 0.950 g (5 mmol) of ethyl di-n-butylphosphinite in 20 ml of toluene and 0.253 g (11 mmol) of sodium in small pieces. The reaction mixture was stirred for 2 hours at 110° C., after which time $^{31}$P NMR showed the presence of sodium dibutylphosphine.

EXAMPLE 19

Preparation of lithio-bis(2-anisyl)phosphine then 1, 3-bis(bis(2-anisyl)phosphino)propane A 100 ml reaction vessel equipped with a mechanical stirrer and a reflux condenser was charged with 3.17 g (10 mmol) of bis(2-anisyl)diethylaminophosphine in 40 ml of THF and 0.146 g (21 mmol) of lithium granules. The reaction mixture was stirred for 16 hours at 10° C. by which time a thick precipitate had formed. $^{31}$P NMR indicated full conversion of the starting phosphine. Next, 1.01 g (5 mmol) of 1 dibromopropane was added. After 2 hours still at 10° C. 20 ml of methanol was added, the solvent was removed under vacuum and 50 ml of dichloromethane and 50 ml of water were added. The organic phase was separated and the aqueous phase, was extracted with 25 ml of dichloromethane. The combined organic layers were washed with 2×25 ml of water, dried on magnesium sulphate, filtered over a P3 glass frit and concentrated to dryness on a rotary evaporator. Upon treatment with 10 ml of methanol the desired diphosphine was obtained in a yield of 1.97 g (74%) as a white solid, which is pure according to $^1$H, $^{13}$C and $^{31}$P NMR.

EXAMPLE 20

Preparation of lithio-bis(2-anisyl)phosphine then 2,2-dimethyl-1,3-bis(bis(2-anisyl)phosphino)propane A 100 ml reaction vessel equipped with a mechanical stirrer and a reflux condenser was charged with 3.17 g (10 mmol) of bis(2-anisyl)diethylaminophosphine in 40 ml of THF and 0.146 g (21 mmol) of lithium granules. There action mixture was stirred for 16 hours at 10° C. by which time a thick precipitate had formed. $^{31}$P NMR indicated full conversion of the starting phosphine. Next 5 ml of DMSO was added followed by slow addition of 1.15 g (5 mmol) of 1,3-dibromo-2,2-dimethylpropane. After 2 hours still at 10° C. 20 ml of methanol was added, the solvent was removed under vacuum and 50 ml of dichloromethane and 50 ml of water were added. The organic phase was separated and the aqueous phase was extracted with 25 ml of dichloromethane. The combined organic layers were washed with 2×25 ml of water, dried on magnesium sulphate, filtered over a P3 glass frit and concentrated to dryness on a rotary evaporator. Upon treatment with 10 ml of methanol the desired phosphine was obtained in a yield of 2.37 g (85%) as a white solid, which is pure according to $^1$H, $^{13}$C and $^{31}$P NMR.

EXAMPLE 21

Comparative: attempted preparation of lithio-bis(2-anisyl)phosphine then 2,2-dimethyl-1,3-bis(bis(2-anisyl)phosphino)propane Example 20 was repeated except that for the second step 0.71 g (5 mmol) of 1,3-dichloro-2,2-dimethylpropane was used instead of the dibromo compound. After 4 hours at 10° C. $^{31}$P NMR analysis of the crude reaction mixture showed the almost exclusive formation of the mono-phosphine compound 2,2-dimethyl-1-(bis-(2-anisyl)-phosphine chloropropane; the desired bis-phosphine was present in less than 5% amount.

EXAMPLE 22

Preparation of lithio-bis(2-anisyl)phosphine then 2,2-diethyl-1,3-bis(bis(2-anisyl)phosphino)propane This diphosphine was prepared by the method of Example 20 in 69% yield.

EXAMPLE 23

Preparation of sodium-bis(2-anisyl)phosphine then 2,2-dimethyl-1,3-bis(bis(2-anisyl)phosphino)propane A 100 ml reaction vessel equipped with a mechanical stirrer and a reflux condenser was charged with 3.17 g (10 mmol) of bis(2-anisyl)diethylaminophosphine in 40 ml of THF and 0.48 g (21 mmol) of sodium in small pieces and 0.27 g (2.1 mmol) of naphthalene. The reaction mixture was stirred for 16 hours at 6° C. after which time $^{31}$P NMR indicated >90° C. conversion of the starting phosphine. Next 5 ml of DMSO was added followed by the slow addition of 1.0 g (4.3 mmol) of 1,3-dibromo-2,2-dimethylpropane. After 2 hours still at 6° C. $^{31}$P NMR showed the conversion of all starting phosphine and quantitative formation of the desired diphosphine.

EXAMPLE 24

Preparation of lithio-diphenylphosphine then 2,2-diethyl-1,3(bis(diphenylphosphino)propane A 100 ml reaction vessel equipped with a mechanical stirrer and a reflux condenser was charged with 2.57 g (10 mmol) of diphenyl(diethylamino)phosphine in 40 ml of THF and 0.146 g (21 mmol) of lithium granules. The reaction mixture was stirred for 16 hours at 10° C. by which time a deep red solution had formed. $^{31}$P NMR indicated full conversion of the starting phosphine to lithium diphenylphosphide. Lithium diethylamide, which was also formed, was quenched by addition of 0.535 g (10 mmol) of ammonium chloride. After stirring for 1 hour 5 ml of DMSO was added followed by slow addition of 1.29 g (5 mmol) of 1,3-dibromo-2,2-diethylpropane, still at 10° C. After conventional work-up the desired diphosphine was obtained in a yield of 1.37 g (59%) as a white solid, which was pure according to $^1$H, $^{13}$C and $^{31}$P NMR.

EXAMPLE 25

Preparation of Quaternary Diphosphonium Salt then 1,3-bis(2-anisylphosphino)propane A mixture of 5.00 g (15.8 mmol) of N,N-diethylamino-bis(2-anisyl)phosphine, 1.59 g (7.89 mmol) of 1,3-dibromopropane and 30 ml of acetonitrile was refluxed. After 18 hours, the solvent was removed and the diphosphonium salt XI confirmed by $^1$H NMR and $^{31}$P NMR. The diphosphonium salt was used without further purification for the next step. To a suspension of 2.00 g (2.4 mmol) of the diphosphonium salt in 20 ml of toluene were added 2.5 ml of sodium bis(2-methoxyethoxy)aluminium dihydride (3.4 M in toluene; 8.5 mmol) over a period of 15 min. The reaction mixture was stirred for 2 hours at ambient temperature then 3 ml of water was added slowly. A $^{31}$P NMR spectrum of the crude reaction mixture showed the complete conversion of the diphosphonium salt and the highly selective formation of the desired diphosphine. The reaction mixture was filtered and the solid residue was extracted with 20 ml of toluene. The combined organic fractions were concentrated in vacuo. Upon recrystallization from methanol the diphosphine was obtained as a white solid which was pure according to $^1$H NMR and $^{31}$P NMR.

EXAMPLE 26

Preparation of Quaternary Diphosphonium Salt then 1 bis(diphenyl)phosphino)propane A mixture of 2.57 g (10 mmol) of N,N-diethylaminodiphenylphosphine, 1.01 g (5 mmol) of 1,3-dibromopropane and 10 ml of acetonitrile was refluxed. After 26 hours the solvent was removed and the diphosphonium salt XI, confirmed by $^{31}$P NMR, was obtained in almost quantitative yield. The diphosphonium salt was used without further purification in the next step. To a suspension of the diphosphonium salt in 20 ml of toluene was added 5 ml of sodium bis(2-methoxyethoxy)aluminium dihydride (3.4 M in toluene; 17 mmol) over a period of 15 min. The reaction mixture was stirred for 2 hours at ambient temperature then 2.5 ml of water was added slowly. A $^{31}$P NMR spectrum of the crude reaction mixture at this point showed the complete conversion of the diphosphonium salt and the almost exclusive formation of the desired diphosphine. The reaction mixture was filtered and the solid residue was extracted with 20 ml of toluene. The combined organic fractions were concentrated in vacuo. Upon treatment with 20 ml of methanol 1.25 g (60%) of the desired diphosphine was obtained, structure confirmed by $^{31}$P NMR.

EXAMPLE 27

Preparation of Quaternary Phosphonium Salt then 1,3-bis(di(n-butyl)phosphino)propane A mixture of 2.17 g (10 mmol) of N,N-diethylamino di(n-butyl)phosphine, 1.01 g (5 mmol) of 1,3-dibromopropane and 10 ml of acetonitrile was refluxed. After 20 hours the solvent was removed and the diphosphonium salt XI, confirmed by $^{31}$P NMR, was obtained in almost quantitative yield. The diphosphonium salt was used without further purification in the next step. To the suspension of diphosphonium salt as prepared above in 20 ml of toluene was added 50 ml of sodium bis(2-methoxy-ethoxy) aluminium dihydride (3.4 M in toluene; 17 mmol) over a period of 5 min. The reaction mixture was stirred for 2 hours at ambient temperature then 2.5 ml of water was added slowly. A $^{31}$P NMR spectrum of the crude reaction mixture at this point showed the complete conversion of the diphosphonium salt and the almost exclusive formation of the desired diphosphine. The reaction mixture was filtered and the solid residue was extracted with 20 ml of toluene. The combined organic fractions were concentrated in vacuo to yield 1.75 g of the desired diphosphine, which was about 90% pure, determined by $^{31}$P NMR. Treatment with methanol yielded the diphosphine which was pure according to $^{1}$H NMR and 31C NMR.

EXAMPLE 28

Preparation of Quaternary Diphosphonium Salt then 1,3-bis(bis(2-anisyl)phosphino)propane The process of Example 27 using lithium aluminium hydride instead of sodium bis(2-methoxyethoxy)aluminium dihydride in the preparation of yielded the title compound, confirmed by $^{1}$H NMR and $^{31}$P NMR.

EXAMPLE 29

Preparation of Quaternary Diphosphonium Salt

A mixture of 2.5 g (7.9 mmol) of N,N-diethylamino-bis (2-anisyl)phosphine, 1.48 g (3.9 mmol) of 1,2-dibromoethane and 15 ml of acetonitrile was refluxed. After 20 hours the solvent was removed and the diphosphonium salt XI was obtained in almost quantitative yield, confirmed by $^{31}$P NMR.

EXAMPLE 30

Preparation of Quaternary Diphosphonium Salt

A quaternary ammonium salt was prepared by the same procedure as that recited for Example 27 except that 1,3-dibromo methylpropane was substituted for 1,3-dibromopropane and the reaction time allowed for the quaternization was 90 hours. The formation of the phosphonium salt XI was confirmed by $^{31}$P NMR.

Biphosphine compounds whose preparation is described above may be used as ligands in the preparation of catalysts for the copolymerization of olefins and carbon monoxide, the catalyst preparation and copolymerization being as generally described earlier in this specification, and as exemplified in many prior patent specifications, for example EP-A-121965 and EP-A Accordingly detailed exemplification is not required here.

We claim:

1. A process for the preparation of a compound of the formula $$R_2P\text{-}L$$

wherein R is hydrocarbyl or substituted hydrocarbyl and L is an amine, alkoxy, aryloxy, alkylthio, or phosphine leaving group, said process comprising:

reacting of a compound of the formula $$R\text{—Li}$$

with a compound of the formula $$Hal_2P\text{-}L$$

wherein Hal represents a halogen atom, in a solvent comprising an ether compound of the formula $$E^1\text{-O-}E^2$$

wherein each of $E^1$ and $E^2$ independently represent an optionally substituted alkyl group or an optionally substituted aryl group, and having a boiling point of at least 40° C. at atmospheric pressure.

2. The process of claim 1 further comprising:

lithiating a compound of the formula $$R\text{—H}$$

wherein R is hydrocarbyl or substituted hydrocarbyl, with a compound of the formula $$Q\text{-Li}$$

wherein Q represents an alkyl, cycloalkyl, aralkyl or aryl group, in a solvent comprising an ether compound of the formula $$E^1\text{-O-}E^2$$

wherein each of $E^1$ and $E^2$ independently represent an optionally substituted alkyl group or an optionally substituted aryl group, and having a boiling point of at least 40° C. at atmospheric pressure to produce a compound of the formula $R^1$—Li; and, reacting said resulting compound with a compound of the formula $$Hal_2P\text{-}L$$

wherein Hal represents a halogen atom and L represents a leaving group, in a solvent comprising an ether compound of the formula $$E^1\text{-O-}E^2$$

wherein each of $E^1$ and $E^2$ independently represent an optionally substituted alkyl group or an optionally substituted aryl group, and having a boiling point of at least 40° C. at atmospheric pressure.

3. The process of claim 1, wherein R is hydrocarbyl substituted with a polar moiety.

4. The process of claim 3, wherein R is aryl substituted with a polar moiety.

5. The process of claim 4, wherein R is a phenyl group that is ortho-substituted with a single polar moiety.

6. The process of claim 3, wherein the polar moiety is selected from the group consisting of halogen, haloalkoxy, alkoxy, amino, monoalkylamino, dialkylamino, aminoalkyl, monoalkyl-aminoalkyl, dialkyl-aminoalkyl, amido, monoalkylamido, dialkylamido, alkoxyalkoxy, alkylthio, alkylsulfonyl, dialkylamidosulfonyl, alkylsulfonate, lithiooxy, aryloxy, sulfonyl, and alkali metal sulfonate.

7. The process of claim 6, wherein the polar moiety is alkoxy or aryloxy.

8. The process of claim 7, wherein the polar moiety is methoxy or phenyloxy.

9. The process of claim 1, wherein L is $-NR''_2$, $-PR''_2$ or $-ZR''$ wherein Z is O or S and R'' is $C_1$–$C_6$ alkyl, or, when L is $-NR''_2$ or $-PR''_2$, the two R'' moieties taken together form an optionally substituted $C_4$–$C_8$ alkylene chain.

10. The process of claim 1, wherein Hal is chloro, bromo or iodo.

* * * * *